United States Patent [19]

Ogawa et al.

[11] Patent Number: 5,945,114
[45] Date of Patent: Aug. 31, 1999

[54] WATER DISPERSIBLE GRANULES

[75] Inventors: Masao Ogawa, Toyonaka; Toshiro Ohtsubo, Sanda; Shigenori Tsuda, Kyoto, all of Japan

[73] Assignee: Sumitomo Chemical Company, Limited, Osaka, Japan

[21] Appl. No.: 07/882,252

[22] Filed: May 8, 1992

Related U.S. Application Data

[63] Continuation of application No. 07/558,454, Jul. 27, 1990, abandoned.

[30] Foreign Application Priority Data

Aug. 2, 1989 [JP] Japan ................................. 1-201559

[51] Int. Cl.⁶ ...................................................... A01N 25/08
[52] U.S. Cl. ......................... 424/408; 424/405; 424/409; 424/421
[58] Field of Search .................... 424/405, 409, 424/724, 417, 421, 408

[56] References Cited

U.S. PATENT DOCUMENTS

| | | | |
|---|---|---|---|
| 3,785,798 | 1/1974 | Horai et al. | 71/79 |
| 4,511,395 | 4/1985 | Misselbrook. | |
| 4,753,957 | 6/1988 | Chan | 514/391 |

FOREIGN PATENT DOCUMENTS

| | | |
|---|---|---|
| 0106164 | 4/1984 | European Pat. Off. . |
| 2645709 | 10/1990 | European Pat. Off. . |
| 2442011 | 6/1980 | France . |
| 354035 | 5/1968 | Spain . |
| 2001339 | 5/1988 | Spain . |
| 1029912 | 5/1966 | United Kingdom . |

OTHER PUBLICATIONS

Winnacker—Kuchler, "Chemische Technologie" Band 7, Organische Technologie III, Carl Hanser Verlag Munchen Wien 1986.

W. Van Valkenburg: "Pesticide formulations", 1973, pp. 186–205, Marcel Dekker, Inc., New York, US.

Patent Abstracts of Japan, vol. 9, No. 119 (C–282) [1842], May 23, 1985; & JP–A–60 011 402 (Tkaeda Yakuhin Kogyo).

Central Patents Index Basic Abstracts Journal, section C, AGDOC, semaine 8440, Nov. 28, 1984, AN=84–246906/40, Derwent Publications Ltd., London, GB; & JP–A–59 148 702 (Shionogi) Aug. 25, 1984.

*Primary Examiner*—Neil S. Levy
*Attorney, Agent, or Firm*—Stevens, Davis, Miller & Mosher, L.L.P.

[57] ABSTRACT

The water dispersible granule of the present invention is obtained by mixing a pesticide having a melting point of not more than 70° C., a calcined product of precipitated hydrated silicon dioxide and a surface active agent, and granulating the resulting mixture by the wet granulation method or compaction method. This water dispersible granule is an excellent formulation of which the physical properties such as disintegrability-in-water, dispersibility, suspensibility, storage stability, etc. are good, and which is free from dust-scattering and is capable of being measured by volume.

3 Claims, No Drawings

WATER DISPERSIBLE GRANULES

This application is Continuation of application Ser. No. 07/558,454 filed Jul. 27, 1990, now abandoned.

The present invention relates to a water dispersible granule superior in disintegration-in-water, suspensibility and storage stability.

Usually, pesticides are used in various formulations, which allow the active ingredient exhibit its efficacy to the maximum by easy and efficient application.

Of these, wettable powders (water dispersible powders) are advantageous in being able to contain a pesticide in high concentrations. However, they have problems that when wettable powders are used or handled, considerable amount of the wettable powders scatter away by air and that the measurement of volume is difficult due to the unevenness of the apparent density.

On the other hand, it has already been known that solid pesticides can be formulated into water dispersible granules. There are several problems, however, in formulating pesticides having a melting point of not more than 70° C. (e.g. pyrethroid insecticides, organophosphorous insecticides) into water dispersible granules; there is a difficulty in formulating pesticides which are liquid at room temperature into water dispersible granules. This difficulty is shared by semi-solid pesticides which have a melting point around room temperature. In addition, even if water dispersible granules were obtained from the semi-solid pesticides, they might have problems as to the storage stability, disintegration-in-water and suspensibility. Further, the same problems are shared by mixed preparations containing a pesticide having a melting point of not more than 70° C. and one having a melting point of more than 70° C.

According to the method of the present invention, excellent water dispersible granules for agricultural purposes are obtained even if they contain pesticides having a melting point of not more than 70° C.

The term "pesticide having a melting point of not more than 70° C." refers to not only a single compound but also a mixture of two or more compounds which mixture shows a melting point of not more than 70° C. (hereinafter the pesticide of lower melting point). The similar interpretation is applied to the term "pesticide having a melting point of more than 70° C." (hereinafter the pesticide of higher melting point).

According to the present invention, there is provided a water dispersible granule obtained by granulating a mixture containing as essential components a pesticide having a melting point of not more than 70° C., a calcined product of precipitated hydrated silicon dioxide and a surface active agent by the wet extrusion-granulation method or compaction method. The mixture optionally comprises one or more members selected from the group consisting of solvents, water-soluble carriers and mineral carriers, or a pesticide having a melting point of more than 70° C. There is also provided a method for producing a water dispersible granule which comprises the steps of mixing a pesticide having a melting point of not more than 70° C., a calcined product of precipitated hydrated silicon dioxide and a surface active agent, and granulating the resulting mixture by the wet extrusion-granulation method or compaction method. The thus obtained water dispersible granule is superior in disintegrability-in-water, suspensibility and storage stability, and is free from the problems such as scaling-off, collapse, etc. of the particles.

The water dispersible granule of the present invention has a particle diameter of 2,000 to 200 μm, preferably 1,500 to 250 μm.

The calcined product of precipitated hydrated silicon dioxide used in the present invention is obtained by calcining synthetic precipitated hydrated silicon dioxide at 700° C. to 900° C. More preffered are those calcined at 800° C. to 900° C. Specific examples of the silica are Tokusil® (produced by Tokuyama Soda Co. Ltd.), Carplex® (produced by Shionogi & Co., Ltd.), Nipsil® (produced by Nippon Silica Inc.), Ultrasil® (produced by Degussa Inc.), etc. Commercially available calcined silica, Carplex® CS-5, Carplex® CS-7, etc. also may be used.

Preferred calcined products of precipitated hydrated silicon dioxide are those having an equilibrium moisture content of 5% or less, an average particle diameter of 5 μm or less and a linseed oil absorption of 2.0 to 3.5 cc/g.

The amount of the calcined product of precipitated hydrated silicon dioxide used is usually 50 to 200% by weight, preferably 70 to 150% by weight based on the liquid component which comprises the pesticide having a melting point of not more than 70° C., a liquid surface active agent and a solvent added as need arises. And the amount is preferably 4 to 40% by weight based on the weight of the whole water dispersible granule.

The surface active agent used in the present invention includes those which can emulsify and disperse the pesticide, the calcined product of precipitated hydrated silicon dioxide, and the other components that are optionally added. For example, it includes anionic surface active agents such as alkylarylsulfonates (e.g. sodium dodecylbenzenesulfonate), alkylnaphthalenesulfonates, sodium salt of naphthalenesulfonic acid/formalin condensate, lignosulfonates, dialkylsulfosuccinates, salts of polyoxyethylene alkylaryl ether sulfuric acid esters, alkali metal salts of carboxyl group-containing copolymers (e.g. GEROPON® SC-211), fatty acid salts; and nonionic surface active agents such as polyoxyethylene alkyl ethers, polyoxyethylene alkylphenyl ethers, polyoxyethylene styrylphenyl ethers, polyoxyethylene alkyl esters, sorbitan alkyl esters, polyoxyethylene sorbitan alkyl esters. Cationic surface active agents and amphoteric surface active agents may also be used if necessary.

These surface active agents are used alone or in mixture of two or more of them.

The amount of the surface active agent used is usually 3 to 40% by weight, preferably 5 to 30% by weight, more preferably 6 to 20% by weight, based on the weight of the whole water dispersible granule.

When the melting point of the pesticide is in a range of 0° to 70° C., a solvent may be added if necessary in order to lower the viscosity at the time of production and further prevent the pesticide from crystallization during low-temperature storage. As the solvent, non-volatile or low-volatility organic solvents are usually used. Such the solvents used for adjusting the viscosity or preventing the crystallization of pesticide include those which are uniformly miscible with the pesticide. For example, they include aromatic hydrocarbons (e.g. phenylxylylethane), ketones, vegetable oils, mineral oils, liquid paraffin, polyethylene glycol which have an average molecular weight of about 200 to about 600 and are liquid at room temperature, polypropylene glycol, glycol ethers such as propylene glycol methyl ether, and the acetates of the glycol ethers. Particularly, phenylxylylethane, glycol ethers and their acetates are preferred. Specific examples thereof are Hisol® SAS-296, Solfit Acetate, Solvesso® 200, etc.

The amount of the solvent added is usually 10 to 1,000% by weight, preferably 30 to 200% by weight, based on the pesticide. If the melting point of the pesticide is not more than 0° C., the foregoing solvents may be added if necessary in order to lower the viscosity at the time of production.

In the present invention, the water-soluble carrier, mineral carrier, etc. may be added in mixing the pesticide, calcined product of precipitated hydrated silicon dioxide, surface active agent, etc. The water-soluble carrier used includes water-soluble polymers such as hydroxypropyl cellulose, methyl cellulose, methylethyl cellulose, polyvinyl alcohol, polyvinyl pyrrolidone, hydroxypropylmethyl cellulose and carboxymethyl cellulose sodium salt; and urea, lactose, ammonium sulfate, sucrose, sodium chloride and sodium sulfate. The mineral carrier includes kaolin clay, diatomite, terra alba, talc, calcium carbonate and attapulgite.

When these water-soluble carrier and/or mineral carrier are added, their amount is usually 0.1 to 85% by weight, preferably 0.5 to 20% by weight based on the weight of the granule.

The water dispersible granules of the present invention may contain a stabilizer, synergist, coloring agent, perfume, builder, etc. in addition to the pesticide, calcined product of precipitated hydrated silicon dioxide, surface active agent, solvent, water-soluble carrier and mineral carrier.

The water dispersible granule of the present invention can be used for controlling harmful insects, acarines and other living organisms and for regulating the growth of plants.

The water dispersible granules of the present invention are used diluted with water to a suitable dilution rate. Although the rate is not critical since it varies depending upon the kind of pesticide, the kind of species of harmful insects, acarines and other living organisms, the plants to which the formulation is applied, the timing of application, the method of application, etc., the rate usually falls within the range of 20–10,000 times.

Specific examples of the pesticide of lower melting point used in the present invention will be shown below, but the present invention is not to be interpreted as being limited thereto.

Compound No. Name of compound
(1) α-Cyano-3-phenoxybenzyl 2-(4-chlorophenyl)-3-methylbutyrate
(2) (S)-α-Cyano-3-phenoxybenzyl (S)-2-(4-chlorophenyl)-3-methylbutyrate
(3) α-Cyano-3-phenoxybenzyl 2,2,3,3-tetramethylcyclopropanecarboxylate
(4) 3-Phenoxybenzyl 3-(2,2-dichlorovinyl)-2,2-dimethylcyclopropanecarboxylate
(5) 3-Phenoxybenzyl chrysanthemate
(6) α-Cyano-3-phenoxybenzyl 3-(2,2-dichlorovinyl)-2,2-dimethylcyclopropanecarboxylate
(7) α-Cyano-3-(4-bromophenoxy)benzyl 3-(2,2-dichlorovinyl)-2,2-dimethylcyclopropanecarboxylate
(8) α-Cyano-3-(4-fluorophenoxy)benzyl 3-(2,2-dichlorovinyl)-2,2-dimethylcyclopropanecarboxylate
(9) α-Cyano-3-(3-bromophenoxy)benzyl 3-(2,2-dichlorovinyl)-2,2-dimethylcyclopropanecarboxylate
(10) α-Cyano-3-(4-chlorophenoxy)benzyl 3-(2,2-dichlorovinyl)-2,2-dimethylcyclopropanecarboxylate
(11) α-Cyano-3-phenoxybenzyl chrysanthemate
(12) α-Cyano-3-(4-bromophenoxy)benzyl 2-(4-chlorophenyl)-3-methylbutyrate
(13) α-Cyano-3-(3-bromophenoxy)benzyl 2-(4-chlorophenyl)-3-methylbutyrate
(14) α-Cyano-3-(4-chlorophenoxy)benzyl 2-(4-chlorophenyl)-3-methylbutyrate
(15) α-Cyano-3-(4-fluorophenoxy)benzyl 2-(4-chlorophenyl)-3-methylbutyrate
(16) α-Cyano-3-phenoxybenzyl 2-(4-bromophenyl)-3-methylbutyrate
(17) α-Cyano-3-phenoxybenzyl 2-(4-tert-butylphenyl)-3-methylbutyrate
(18) α-Cyano-3-phenoxybenzyl 2-(3,4-methylenedioxyphenyl)-3-methylbutyrate
(19) α-Cyano-(4-fluoro-3-phenoxy)benzyl 3-(2,2-dichlorovinyl)-2,2-dimethylcyclopropanecarboxylate
(20) α-Cyano-3-phenoxybenzyl 2-(2-chloro-4-trifluoromethylanilino)-3-methylbutyrate
(21) α-Cyano-3-phenoxybenzyl 2-(4-difluoromethoxyphenyl)-3-methylbutyrate
(22) α-Cyano-(5-phenoxy-2-pyridyl)methyl 3-(2,2-dichlorovinyl)-2,2-dimethylcyclopropanecarboxylate
(23) α-Cyano-3-phenoxybenzyl 2,2-dimethyl-3-(1,2,2,2-tetrabromoethyl)cyclopropanecarboxylate
(24) α-Cyano-3-phenoxybenzyl 2,2-dimethyl-3-(1,2-dichloro-2,2-dibromoethyl)cyclopropanecarboxylate
(25) α-Cyano-3-phenoxybenzyl 1-(4-ethoxyphenyl)-2,2-dichlorocyclopropanecarboxylate
(26) α-Cyano-3-phenoxybenzyl 2,2-dimethyl-3-(2-chloro-3-trifluoromethylvinyl)cyclopropanecarboxylate
(27) 2-(4-Ethoxyphenyl)-2-methylpropyl 3-phenoxybenzyl ether
(28) 3-Phenoxybenzyl 2-(4-ethoxyphenyl)-3,3,3-trifluoropropyl ether
(29) 2-Methyl-3-phenylbenzyl (1R, trans)-2,2-dimethyl-3-(2-chloro-2-trifluoromethylvinyl)cyclopropanecarboxylate
(30) 2,3,5,6-Tetrafluoro-4-methylbenzyl (1R, trans)-2,2-dimethyl-3-(2-chloro-2-trifluoromethylvinyl)cyclopropanecarboxylate
(31) 3,4,5,6-Tetrahydrophthalimidomethyl chrysanthemate
(32) 3,4,5,6-Tetrahydrophthalimidomethyl (1R)-chrysanthemate
(33) 3-Allyl-2-methyl-4-oxocyclopent-2-enyl chrysanthemate
(34) 3-Allyl-2-methyl-4-oxocyclopent-2-enyl (1R)-chrysanthemate
(35) (S)-2-Methyl-4-oxo-3-(2-propynyl)cyclopent-2-enyl (1R)-chrysanthemate
(36) 1-Ethynyl-2-methyl-2-pentenyl (1R)-chrysanthemate
(37) 5-Benzyl-3-furylmethyl chrysanthemate
(38) 5-Benzyl-3-furylmethyl (1R)-chrysanthemate
(39) O,O-Dimethyl-O-(3-methyl-4-nitrophenyl) phosphorothioate
(40) O,O-Dimethyl-S-[1,2-di(ethoxycarbonyl)ethyl] phosphorodithioate
(41) O,O-Dimethyl-O-(4-cyanophenyl)phosphorothioate
(42) O,O-Dimethyl-S-(α-ethoxycarbonylbenzyl) phosphorodithioate
(43) O,O-Diethyl-O-(2-isopropyl-4-methyl-6-pyrimidinyl) phosphorothioate
(44) O,O-Dimethyl-O-[3-methyl-4-(methylthio)phenyl] phosphorothioate
(45) O-(4-Bromo-2,5-dichlorophenyl)-O,O-diethylphosphorothioate
(46) 2-Methoxy-4H-1,3,2-benzodioxaphosphorine-2-sulfide
(47) O,O-Dimethyl-O-(2,4,5-trichlorophenyl) phosphorothioate
(48) O,O-Diethyl-O-(3,5,6-trichloro-2-pyridyl) phosphorothioate
(49) O,O-Dimethyl-O-(3,5,6-trichloro-2-pyridyl) phosphorothioate
(50) O-(4-Bromo-2,5-dichlorophenyl)-O,O-dimethylphosphorothioate
(51) O,O-Dimethyl-S-(N-methylcarbamoylmethyl) phosphorodithioate

(52) 2-sec-Butylphenyl N-methylcarbamate
(53) 3-Methylphenyl N-methylcarbamate
(54) 3,4-Dimethylphenyl N-methylcarbamate
(55) 2-Isopropoxyphenyl N-methylcarbamate
(56) 5-Ethoxy-3-trichloromethyl-1,2,4-thiadiazole
(57) O,O-Diisopropyl-S-benzyl phosphorothiolate
(58) O-Ethyl-S,S-diphenyldithiophosphate
(59) Polyoxin
(60) Plasticidine S
(61) 3,4-Dichloropropionanilide
(62) Isopropyl N-(3-chlorophenyl)carbamate
(63) Ethyl-di-n-propylthiocarbamate
(64) 3-Methoxycarbonylaminophenyl N-(3-methylphenyl)carbamate
(65) 2-Chloro-(2,6-diethyl-N-methoxymethyl)acetanilide
(66) α,α,α-Trifluoro-2,6-dinitro-N,N-dipropyl-p-toluidine
(67) S-(4-Chlorophenyl)methyl-N,N-diethylthiolcarbamate
(68) S-Ethylhexahydro-1H-azepin-1-carbothioate
(69) N-Butoxymethyl-2-chloro-(2,6-diethylacetanilide)
(70) O-Ethyl-O-(5-methyl-2-nitrophenyl)-sec-butylphosphoroamidothioate
(71) N-(Chloroacetyl)-N-(2,6-diethylphenyl)glycine ethyl ester
(72) 2-[1 Methyl-2-(4-phenoxyphenoxy)ethoxy]pyridine These pesticides are contained in the water dispersible granule in an amount of usually 5 to 50% by weight, preferably 10 to 40% by weight. In the present invention, the content of the liquid components including the pesticide of lower melting point, a liquid surface active agent and optionally an organic solvent is usually 5 to 60% by weight, preferably 10 to 50% by weight based on the weight of the water dispersible granule. When the content exceeds 60% by weight, the content of the calcined product of precipitated hydrated silicon dioxide used for absorption of the pesticides etc. has to be reduced, so that the resulting mixture before the granulation tends to become easy to get wet and it is difficult to granulate this mixture. When the content is less than 5% by weight, the resulting water dispersible granule, due to the low active ingredient content, tends to become inefficient for agricultural use.

The water dispersible granule of the present invention may contain a pesticide having a melting point of more than 70° C. depending upon uses. Specific examples of the pesticides of higher melting point will be shown below, but the present invention is not to be interpreted as being limited thereto.

Compound No. Name of compound
(73) (E)-1-(4-Chlorophenyl)-4,4-dimethyl-2-(1H-1,2,4-triazol-1-yl)-1-penten-3-ol
(74) 1-(4-Chlorophenyl)-4,4-dimethyl-2-(1H-1,2,4-triazol-1-yl)pentan-3-ol
(75) N-(1,1,3-Trimethyl-2-oxa-4-indanyl)-5-chloro-1,3-dimethylpyrazol-4-carboxamide
(76) (RS)-2-Bromo-N-(α,α-dimethylbenzyl)-3,3-dimethylbutyramide
(77) N-(3,5-Dichlorophenyl)-1,2-dimethylcyclopropane-1,2-dicarboximide
(78) 1-(4-Chlorophenyl)-3-(2,6-difluorobenzoyl)urea
(79) 1-Ethyl-1,4-dihydro-6,7-methylenedioxy-4-oxo-3-quinolinecarboxylic acid
(80) (E)-1-(2,4-Dichlorophenyl)-4,4-dimethyl-2-(1,2,4-triazol-1-yl)-1-penten-3-ol
(81) Isopropyl 3,4-diethoxyphenylcarbamate
(82) N-[4-Chloro-2-fluoro-5-{(1-methyl-2-propynyl)oxy}phenyl]-3,4,5,6-tetrahydrophthalimide
(83) Pentyl 2-chloro-4-fluoro-5[(3,4,5,6-tetrahydro)phthalimido]phenoxyacetate
(84) 7-Fluoro-6-[(3,4,5,6-tetrahydro)phthalimido]-4-(2-propynyl)-1,4-benzoxazine-3(2H)-one When these pesticides of higher melting point are used, their amount is usually 0.1 to 60% by weight, preferably 1 to 50% by weight based on the weight of the water dispersible granule. The sum of the amounts of the pesticide of lower melting point and the pesticide of higher melting point is usually 5 to 65% by weight, preferably 10 to 50% by weight, based on the weight of the water dispersible granule.

The water dispersible granules of the present invention are produced, for example, as follows:

A pesticide of lower melting point is heated to 40° to 80° C. If necessary, a solvent is added thereto. Then, a calcined product of precipitated hydrated silicon dioxide is added so as to absorb the pesticide (and the solvent). Thereafter, to the mixture of pesticide and silica are added a surface active agent and, if necessary, a water-soluble carrier and/or a mineral carrier. After they had been thoroughly mixed, the resulting mixture is kneaded with water or a polymer solution in water, extrusion-granulated with a granulator equipped with a 0.5 to 1.5 mmΦ screen, dried and sieved to obtain a water dispersible granule. Alternatively, the water dispersible granule can also be obtained, instead of carrying out the kneading and extrusion-granulation, by shaping the mixture as it is without adding water into sheet-like or pillow-like granulates, tablets or slugs with a compacting machine (e.g. roller compacters, briquetting machines) or with a tableting machine and breaking the granulates or slugs with a particle size-regulator. In the case a compacting machine is used, the mixture is fed between the rotating rollers, and a pressure of 30 kg/cm$^2$ or more, preferably 50 kg/cm$^2$ or more is applied.

A water dispersible granule containing a pesticide of higher melting point can be obtained in the same manner as above. In this case, a pulverized product of the pesticide of higher melting point is mixed with the pesticide of lower melting point before the addition of the calcined product of precipitated hydrated silicon dioxide. Alternatively, the pesticide of higher melting point is mixed with the calcined product of precipitated hydrated silicon dioxide, the mixture is pulverized and the pulverized mixture is mixed with the pesticide of lower melting point.

The water dispersible granules of the present invention have good physical properties, for example excellent disintegration-in-water and suspensibility (dispersibility-in-water), although a high pressure has been applied to them at the time of granulation with a wet extrusion-granulator or with a compacting machine.

The present invention will be illustrated in more detail with reference to the following production examples and test examples, but the present invention is not to be interpreted as being limited thereto.

In the following production examples, parts are by weight. The compounds are shown by the foregoing Compound No.

Production Example 1

Ten parts of Compound (3) and 20 parts of Hisol® SAS-296 (phenylxylylethane, an organic solvent produced by Nippon Petrochemicals Co., Ltd.) were mixed together while warming them at about 50° C. To the resulting mixture was added a mixture of 20 parts of a spray-dried product of 1:1 mixture of sodium dodecylbenzenesulfonate and Carplex® CS-7 (calcined product of precipitated hydrated silicon dioxide produced by Shionogi & Co., Ltd., equilibrium moisture content: 1.80%, average particle diameter measured by means of coal tar counter: 2.8 μm, linseed oil absorption: 2.34 cc/g), which is a powdery product obtained by dispersing Carplex® CS-7 in an aqueous solution of sodium dodecylbenzenesulfonate and spray-drying the resulting dispersion with a spray-drier, 3 parts of sodium salt of a naphthalenesulfonic acid/formalin condensate, 15 parts of Carplex® CS-7 and 31.5 parts of α-hydrated lactose. Thereafter, 10 parts of 5% aqueous solution of hydroxypropyl cellulose (viscosity: 6 to 10 centipoises at 20° as a 2% aqueous solution) was added thereto. The resulting mixture was well kneaded and granulated with a horizontal-type extrusion-granulator equipped with a 0.5 mmφ screen (produced by Hata Iron Works Co., Ltd.). The granulates were dried at 60° C. for 10 minutes and sieved to obtain a water dispersible granule having a particle diameter of 1,000 to 297 μm.

Production Example 2

Ten parts of Compound (3) and 20 parts of Hisol® SAS-296 were mixed together while warming them at about 50° C. to the resulting mixture was added a mixture of 4 parts of a spray-dried product of 1:1 mixture of sodium dodecylbenzenesulfonate and Carplex® CS-7, 16 parts of GEROPON® SC-211 (sodium salt of a carboxyl group-containing copolymer produced by Rhône-Poulenc S.A.), 20 parts of Carplex® CS-7 and 29.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 60° C. for 10 minutes and sieved to obtain a water dispersible granule having a particle diameter of 1,000 to 297 μm.

Production Example 3

A water dispersible granule having a particle diameter of 1,410 to 350 μm was obtained in the same manner as in Production Example 2 except that the 0.5 mmφ screen mounted on the horizontal-type extrusion-granulator was replaced by a 0.9 mmφ screen.

Production Example 4

15 Parts of Compound (3) and 30 parts of Hisol® SAS-296 were mixed together while warming them at about 50° C. To the resulting mixture was added a mixture of 20 parts of a spray-dried product of 1:1 mixture of sodium dodecylbenzenesulfonate and Carplex® CS-7, 5 parts of sodium salt of a naphthalenesulfonic acid/formalin condensate, 22 parts of Carplex® CS-7 and 7.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 60° C. for 10 minutes and sieved to obtain a water dispersible granule having a particle diameter of 1,000 to 297 μm.

Production Example 5

15 Parts of Compound (3) and 30 parts of Hisol® SAS-296 were mixed together while warming them at about 50° C. To the resulting mixture was added a mixture of 20 parts of a spray-dried product of 1:1 mixture of sodium dodecylbenzenesulfonate and Carplex® CS-7, 5 parts of sodium salt of a naphthalenesulfonic acid/formalin condensate and 29.5 parts of Carplex® CS-7. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 60° C. for 10 minutes and sieved to obtain a water dispersible granule having a particle diameter of 1,000 to 297 μm.

Production Example 6

20 Parts of Compound (3) and 20 parts of Solfit Acetate (acetic acid ester of polypropylene glycol ether produced by Kuraray Co., Ltd.) were mixed together while warming them at about 50° C. To the resulting mixture was added a mixture of 20 parts of a spray-dried product of 1:1 mixture of sodium dodecylbenzenesulfonate and Carplex® CS-7, 3 parts of sodium salt of a naphthalenesulfonic acid/formalin condensate, 20 parts of Carplex® CS-7 and 16.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 40° C. for 10 minutes and sieved to obtain a water dispersible granule having a particle diameter of 1,000 to 297 μm.

Production Example 7

20 Parts of Compound (3) and 25 parts of Solfit Acetate were mixed together while warming them at about 50° C. To the resulting mixture was added a mixture of 20 parts of a spray-dried product of 1;1 mixture of sodium dodecylbenzenesulfonate and Carplex® CS-7, 3 parts of sodium salt of a naphthalenesulfonic acid/formalin condensate, 22 parts of Carplex® CS-7 and 9.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 40° C. for 10 minutes and sieved to obtain a water dispersible granule having a particle diameter of 1,000 to 297 μm.

Production Example 8

20 Parts of Compound (3) and 30 parts of Solfit Acetate were mixed together while warming them at about 50° C. To the resulting mixture was added a mixture of 2 parts of a spray-dried product of 1:1 mixture of sodium dodecylbenzenesulfonate and Carplex® CS-7, 8 parts of GEROPON® SC-211 and 39.5 parts of Carplex® CS-7. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 40° C. for 10 minutes and sieved to obtain a water dispersible granule having a particle diameter of 1,000 to 297 μm.

Production Example 9

20 Parts of Compound (3) and 30 parts of Solvesso® 200 (alkylnaphthalene produced by Exxon Corp.) were mixed together while warming them at about 50° C. To the resulting mixture was added a mixture of 20 parts of a spray-dried product of 1:1 mixture of sodium dodecylbenzenesulfonate and Carplex® CS-7, 3 parts of sodium salt of a naphthalenesulfonic acid/formalin condensate and 27 parts of Carplex® CS-7. The resulting mixture was well kneaded and granulated with a horizontal-type extrusion-granulator equipped with a 0.5 mmφ screen. The granulates were sieved to obtain a water dispersible granule having a particle diameter of 1,000 to 297 μm.

Production Example 10

10 Parts of Compound (3) and 20 parts of Hisol® SAS-296 were mixed together while warming them at about 50° C. To the resulting mixture was added a mixture of 10 parts of a spray-dried product of 1:1 mixture of sodium dodecylbenzenesulfonate and Carplex® CS-7, 3 parts of sodium salt of a naphthalenesulfonic acid/formalin condensate, 22 parts of Carplex® CS-7 and 35 parts of α-hydrated lactose. The resulting mixture was well kneaded and granulated into sheet-like granulates under a pressure of 150 kg/cm$^2$ on Roller Compacter TF Mini-type (compacting machine produced by Freund Industrial Co., Ltd.). The resulting granulates were broken using a mortar and pestle and sieved to obtain a water dispersible granule having a particle diameter of 710 to 297 μm.

Production Example 11

To 40 parts of Compound (39) was added a mixture of 20 parts of a spray-dried product of 1:1 mixture of sodium dodecylbenzenesulfonate and Carplex® CS-7, 3 parts of sodium salt of a naphthalenesulfonic acid/formalin condensate, 20 parts of Carplex® CS-7 and 16.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 40° C. for 10 minutes and sieved to obtain a water dispersible granule having a particle diameter of 1,000 to 297 μm.

Production Example 12

Ten parts of Compound (3) and 20 parts of Hisol® SAS-296 were mixed together while warming them at about 50° C. To the resulting mixture was added a mixture of 4 parts of a spray-dried product of 1:1 mixture of sodium dodecylbenzenesulfonate and Carplex® CS-7, 16 parts of GEROPON® SC-211, 20 parts of Carplex® CS-7 and 26.5 parts of α-hydrated lactose. Thereafter, a pulverized mixture of 2.5 parts of Compound (80) and 0.5 part of Carplex® CS-7 was added thereto. Thereafter, 10 parts of 5% aqueous solution of hydroxypropyl cellulose was added, and the resulting mixture was well kneaded and granulated with a horizontal-type extrusion-granulator equipped with a 0.5 mmφ screen. The granulates were dried at 40° C. for 15 minutes and sieved to obtain a water dispersible granule having a particle diameter of 1,000 to 297 μm.

Comparative Example 1

Ten parts of Compound (3) and 20 parts of Hisol® SAS-296 were mixed together while warming them at about 50° C. To the resulting mixture was added a mixture of 20 parts of a spray-dried product of 1:1 mixture of sodium dodecylbenzenesulfonate and Carplex® #80 (uncalcined silica (precipitated hydrated silicon dioxide) produced by Shionogi & Co., Ltd.), which is a powdery product obtained by dispersing Carplex® #80 in an aqueous solution of sodium dodecylbenzenesulfonate and spray-drying the resulting dispersion with a spray drier, 3 parts of sodium salt of a naphthalenesulfonic acid/formalin condensate, 15 parts of Carplex® #80 and 31.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 60° C. for 10 minutes and sieved to obtain a water dispersible granule having a particle diameter of 1,000 to 297 μm.

Comparative Example 2

Ten parts of Compound (3) and 20 parts of Hisol® SAS-296 were mixed together while warming them at about 50° C. To the resulting mixture was added a mixture of 4 parts of a spray-dried product of 1:1 mixture of sodium dodecylbenzenesulfonate and Carplex® #80, 16 parts of GEROPON® SC-211, 20 parts of Carplex® #80 and 29.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 60° C. for 10 minutes and sieved to obtain a water dispersible granule having a particle diameter of 1,000 to 297 μm.

Comparative Example 3

30 Parts of Compound (3) was warmed to about 60° C. Thereto was added a mixture of 20 parts of a spray-dried product of 1:1 mixture of sodium dodecylbenzenesulfonate and Carplex® #80, 3 parts of sodium salt of a naphthalenesulfonic acid/formalin condensate, 20 parts of Carplex® #80 and 26.5 parts of α-hydrated lactose. After adding thereto 10 parts of 5% aqueous solution of hydroxypropyl cellulose (the same as above), the resulting mixture was well kneaded and granulated with a horizontal-type extrusion-granulator equipped with a 0.5 mmφ screen. The granulates were dried at 60° C. for 10 minutes and sieved to obtain a water dispersible granule having a particle diameter of 1,000 to 297 μm.

Comparative Example 4

To 40 Parts of Compound (39) was added a mixture of 20 parts of a spray-dried product of 1:1 mixture of sodium dodecylbenzenesulfonate and Carplex® #80, 3 parts of sodium salt of a naphthalenesulfonic acid/formalin condensate, 20 parts of Carplex® #80 and 16.5 parts of α-hydrated lactose. Thereafter, 10 parts of 5% aqueous solution of hydroxypropyl cellulose (the same as above) was added thereto. The resulting mixture was well kneaded and granulated with a horizontal-type extrusion-granulator equipped with a 0.5 mmφ screen. The granulates were dried at 40° C. for 10 minutes and sieved to obtain a water dispersible granule having a particle diameter of 1,000 to 297 μm.

Comparative Example 5

Ten parts of Compound (3) and 20 parts of Hisol® SAS-296 were mixed together while warming them at about 50° C. To the resulting mixture was added a mixture of 4 parts of a spray-dried product of 1:1 mixture of sodium dodecylbenzenesulfonate and Carplex® CS-7, 16 parts of GEROPON® SC-211, 20 parts of Carplex® CS-7 and 30 parts of α-hydrated lactose. The mixture obtained were well mixed to give a wettable powder (water dispersible powder).

Test Example 1

About 5 g each of the water dispersible granule obtained in Production Examples 1, 2 and 3 and Comparative Example 1, 2 and 3 was put into an aluminum foil bag and stored at 0° C. for 30 days or at 40° C. for 30 days.

The solubility (the number of repetition of upside-down turning of the cylinder required to completely disintegration-disperse the water dispersible granule) and the suspensibility were determined for the water dispersible granule after storage and the corresponding ones immediately after the production.

The determination methods are as follows: 250 Milliliters of 3° hard water were put in 250-ml cylinders with a group stopper. The cylinders were placed in a constant-temperature water bath kept at 20° C. Thereafter, 500 mg each of the above water dispersible granules was put in the cylinder which was then turned upside down. This upside-down turning was repeated at a rate of once per 2 seconds. The solubility was expressed by the number of repetition of upside-down turning of the cylinder required to completely disintegration-disperse the water dispersible granule. The number of repetition of upside-down turning was limited to 30. Thereafter, the cylinders were allowed to stand still in the constant-temperature water bath kept at 20° C. After 15 minutes, 25 ml of the solution was sampled with a pipette from the central portion of each cylinder. The solution was concentrated with a rotary evaporator, and analyzed by gas chromatography to obtain the suspensibility.

The results are shown in Tables 1 and 2.

TABLE 1

| | Solubility (number of repetition of upside-down turning) | | |
|---|---|---|---|
| | Immediately after production | After storage at 0° C. for 30 days | After storage at 40° C. for 30 days |
| Production Example 1 | 4 | 11 | 5 |
| Production Example 2 | 5 | 6 | 5 |
| Production Example 3 | 15 | 20 | 19 |
| Comparative Example 1 | >30 | >30 | >30 |
| Comparative Example 2 | >30 | >30 | >30 |
| Comparative Example 3 | >30 | >30 | >30 |

TABLE 2

| | Suspensibility (%) | | |
|---|---|---|---|
| | Immediately after production | After storage at 0° C. for 30 days | After storage at 40° C. for 30 days |
| Production Example 1 | 89.7 | 81.6 | 83.7 |
| Production Example 2 | 100.0 | 100.0 | 94.6 |
| Production Example 3 | 97.1 | 96.9 | 87.3 |
| Comparative Example 1 | 65.6 | 60.4 | 54.2 |
| Comparative Example 2 | 70.7 | 64.3 | 61.4 |
| Comparative Example 3 | 47.4 | 1.4 | 33.1 |

As shown in Tables 1 and 2, the water dispersible granules of the present invention are excellent in the solubility, suspensibility and storage stability at low ambient temperatures and high ambient temperatures.

Test Example 2

The solubility and the suspensibility were determined in the same manner as in Test Example 1 for the water dispersible granules immediately after production obtained in Production Examples 4 to 11 and Comparative Example 4.

The results are shown in Table 3.

TABLE 3

| | Solubility (number of repetition of upside-down turning) | Suspensibility (%) |
|---|---|---|
| Production Example 4 | 3 | 95.9 |
| Production Example 5 | 7 | 89.8 |
| Production Example 6 | 12 | 96.3 |
| Production Example 7 | 5 | 94.2 |
| Production Example 8 | 2 | 96.2 |
| Production Example 9 | 8 | 81.7 |
| Production Example 10 | 14 | 92.3 |
| Production Example 11 | 7 | 87.6 |
| Comparative Example 4 | >30 | 53.5 |

As shown in Table 3, the water dispersible granules of present invention are excellent in the solubility and suspensibility.

Test Example 3

20 Grams each of the water dispersible granules obtained in Production Examples 1, 2 and 3 was put in a 250-ml polyethylene bottle and shaken 30 times by hand. Thereafter, the bottle was opened, and the state of dust-scattering and collapse of particle were observed. However, no dust-scattering, collapse nor scaling-off of the particles were observed in any of the water dispersible granules.

In contrast, in the same test using the wettable powder obtained in Comparative Example 5, considerable dust-scattering was observed.

Text Example 4

One hundred milliliters of each of the water dispersible granule prepared in Production Example 2 and the wettable powder prepared in Comparative Example 5 was packed in a 100 ml-cylinder. The apparent density was determined. The determination was repeated five times. Table 4 shows the results.

TABLE 4

| | Apparent density (g/cc) | | | | |
|---|---|---|---|---|---|
| | 1st | 2nd | 3rd | 4th | 5th |
| Production Example 2 | 0.54 | 0.54 | 0.54 | 0.54 | 0.54 |
| Comparative Example 5 | 0.19 | 0.23 | 0.20 | 0.26 | 0.17 |

As shown in Table 4, the apparent density data of the water dispersible granule of Production Example 2 were constant even though the determination was repeated five times. The granule can be measured by volume at the time of dilution. By contrast, the apparent density data of the wettable powder of Comparative Example 5 varied too widely to rely upon the measurement by volume.

Reference Example (controlling test against two-spotted spider mite)

A proper number of two-spotted spider mites (*Tetranychus urticae*, Py-S strain) was inoculated to a kidney bean planted in a pot. The bean was allowed to stand for four days.

The water dispersible granule prepared in Production Example 2 was diluted with water to obtain a solution having 50 ppm of the active ingredient and a solution having 100 ppm of the active ingredient. Forty milliliters of each of the solution was uniformly sprayed onto three pots of the kidney bean. The pots were allowed in a greenhouse kept warm.

The mites were counted before the application of the solution and at 3, 7, 14, 22 and 28 days after the application. Table 5 show the results.

TABLE 5

| Production Example 2 | Number of mites per three pots | | | | | |
|---|---|---|---|---|---|---|
| | Before appln | 3 Days after appln | 7 Days after appln | 14 Days after appln | 22 Days after appln | 28 Days after appln |
| 50 ppm* | 82 | 0 | 0 | 12 | 80 | 177 |
| 100 ppm* | 82 | 0 | 0 | 3 | 20 | 85 |
| No treatment | 81 | 79 | 125 | 156 | 469 | 833 |

*Concentration of the active ingredient in the applied solution

The water dispersible granule of the present invention is an excellent formulation of which the physical properties such as disintegrability-in-water, dispersibility, suspensibility, storage stability, etc. are good, and which is free from dust-scattering and is capable of being measured by volume.

What is claimed is:

1. A water dispersible granule which is obtained by granulating a mixture comprising a pyrethroid insecticide having a melting point of not more than 70° C., a calcined product of precipitated hydrated silicon dioxide and a surface active agent by wet extrusion-granulation method or compaction method, wherein the mixture further comprises at least one member selected from the group consisting of solvents, water-soluble carriers and mineral carriers, the content of the pyrethroid insecticide in the granule is 5 to 50% by weight, that of the calcined product of precipitated hydrated silicon dioxide is 4 to 40% by weight and that of the surface active agent is 5 to 30% by weight and (i) in the case where the mixture comprises at least one solvent, the amount of the solvent is 10–1000% by weight based on the pyrethroid insecticide, and (ii) in the case the mixture comprises at least one carrier selected from the group consisting of water-soluble carrier and mineral carrier the amount is 0.1 to 85% by weight based on the weight of the granule.

2. The water dispersible granule of claim 1, which further comprises a pyrethroid insecticide having a melting point of more than 70° C.

3. The water dispersible granule of claim 2, which comprises 5 to 50% by weight of the pyrethroid insecticide having a melting point of not more than 70° C., 0.1 to 60% by weight of the pyrethroid insecticide having a melting point of more than 70° C., 4 to 40% by weight of the calcined product of precipitated hydrated silicon dioxide and 5 to 30% by weight of the surface active agent.

* * * * *